US006696028B2

(12) United States Patent
Bara

(10) Patent No.: US 6,696,028 B2
(45) Date of Patent: Feb. 24, 2004

(54) BIOLOGICAL ANALYSIS SYSTEM COMPRISING A MEANS FOR CONTROLLING THE LINK BETWEEN A BIOLOGICAL ANALYSIS DEVICE AND A COMPLEMENTARY RECEPTACLE

(75) Inventor: Nicolas Bara, La Villertertre (FR)

(73) Assignee: Central Labo Europe S.A.R.L. (FR)

( * ) Notice: Subject to any disclaimer, the term of this patent is extended or adjusted under 35 U.S.C. 154(b) by 17 days.

(21) Appl. No.: 09/872,148

(22) Filed: Jun. 1, 2001

(65) Prior Publication Data

US 2001/0055800 A1 Dec. 27, 2001

Related U.S. Application Data

(63) Continuation of application No. PCT/FR99/03023, filed on Dec. 6, 1999.

(30) Foreign Application Priority Data

Dec. 9, 1998 (FR) ............................................ 98 15535

(51) Int. Cl.[7] ............................. A61L 2/00; A61L 9/00
(52) U.S. Cl. ..................................................... 422/299
(58) Field of Search ........................................ 422/299

(56) References Cited

U.S. PATENT DOCUMENTS 4,724,427 A * 2/1988 Carroll ................... 340/572.1
5,566,441 A * 10/1996 Marsh et al. ................. 29/600
5,930,145 A * 7/1999 Yuyama et al. ............. 700/231
5,961,925 A * 10/1999 Ruediger et al. ............. 422/99
6,475,443 B1 * 11/2002 van Deursen et al. ...... 422/102

FOREIGN PATENT DOCUMENTS

| EP | 0 875 292 A1 | 11/1998 |
| GB | 2 129 551 A | 5/1984 |

* cited by examiner

*Primary Examiner*—Mark L. Bell
*Assistant Examiner*—Jennine Brown
(74) *Attorney, Agent, or Firm*—Piper Rudnick LLP

(57) ABSTRACT

A biological analysis system including at least one receptacle of a biological sample to be analyzed, a part associated with the receptacle incorporating an electronic circuit including a memory and a contactless transmitter, and a biological analysis device including a receiver circuit, a comparator, and means to prevent operation in the absence of positive detection of a sample linked to an analysis, storage or operation to be performed, with positive detection being linked to an identification zone smaller than about 20 cm, wherein the comparator compares data transmitted by an electronic circuit incorporated in the part, with data transmitted by the circuit incorporated in the part pertaining to the analysis, storage or operation to be performed.

12 Claims, No Drawings

BIOLOGICAL ANALYSIS SYSTEM COMPRISING A MEANS FOR CONTROLLING THE LINK BETWEEN A BIOLOGICAL ANALYSIS DEVICE AND A COMPLEMENTARY RECEPTACLE

RELATED APPLICATION

This is a continuation of International Application No. PCT/FR99/03023, with an international filing date of Dec. 6, 1999, which is based on French Patent Application No. 98/15535, filed Dec. 9, 1998.

FIELD OF THE INVENTION

This invention pertains to the field of biological analysis and medical diagnosis.

BACKGROUND

Errors in the identification of biological samples can lead to grave consequences. The traceability of a sample to be analyzed is thus an essential criterion for an analysis system. In order to avoid errors, it is known to label the sample supports with identification codes, especially bar codes.

This solution is not completely satisfactory. It requires reading bar codes for each sample, which leads to a loss of time and additional handling. Furthermore, the bar code is printed on a label which can deteriorate and thus make identification difficult, subject to error or impossible. Finally, the bar code can only contain a relatively limited amount of information and it is easily forgeable.

Also known are European patents EP 706825, EP 875292, EP 637750 and the British patent GB 2129551. These documents of the prior art divulge analysis systems or components of such systems that employ an electronic circuit with a contactless transmitter and a device comprising a receiver circuit and means for comparison with the data transmitted by the electronic circuit incorporated in the part.

Thus, it would be advantageous to provide a reliable process which does not require additional handling for reading an identifier and which enables automation of the verification as well as an absolute identification.

SUMMARY OF THE INVENTION

This invention relates to a biological analysis system including at least one receptacle of a biological sample to be analyzed, a part associated with the receptacle incorporating an electronic circuit including a memory and a contactless transmitter, and a biological analysis device including a receiver circuit, a comparator, and means to prevent operation in the absence of positive detection of a sample linked to an analysis, storage or operation to be performed, with positive detection being linked to an identification zone smaller than about 20 cm, wherein the comparator compares data transmitted by an electronic circuit incorporated in the part, with data transmitted by the circuit incorporated in the part pertaining to the analysis, storage or operation to be performed.

The invention also relates to an analysis receptacle intended for use in the analysis system including a molded plastic microplate incorporating in its mass a circuit including a transmitter and a memory and an analysis device intended for use in the analysis system including a receiver for receiving signals transmitted by a receiver present in a detection zone.

DETAILED DESCRIPTION

This invention pertains to a biological analysis system comprising a control function for linking a biological analysis device and at least one receptacle of a biological sample to be analyzed, characterized in that it comprises at least one receptacle constituted of a part incorporating an electronic circuit comprising a memory and a contactless transmitter, and at least one device comprising a receiver circuit and means for comparison between the data transmitted by the electronic circuit incorporated in the part possibly present in the detection zone and the data pertaining to the analysis, storage or operation to be performed.

The receptacle is advantageously a molded plastic part comprising an electronic circuit incorporated in its mass. The electronic circuit incorporated in the receptacle for the sample to be analyzed is preferably constituted of an integrated circuit, generally referred to as a radio-frequency label.

According to one variant, the electronic circuit incorporated in the receptacle of the sample to be analyzed includes an induction loop for powering the electronic circuit. According to another variant, the electronic circuit also includes a receiver intended to receive personalization information recorded in the electronic memory. The analysis equipment advantageously comprises means to prevent its operation in the absence of positive detection of the sample linked to the analysis, storage or operation to be performed.

According to one variant, the analysis device comprises means for reading the signals transmitted by the receptacle to provide the results of the analysis. The identification zone is preferable smaller than about 20 cm.

The invention also comprises a molded plastic microplate incorporating in its mass a circuit comprising a transmitter and a memory. The invention further preferably comprises a receiver for receiving signals transmitted by a receiver present in the detection zone.

Better understanding of the invention will be obtained by reading the description below regarding a nonlimitative example of implementation.

According to one example of implementation, the system is composed of microplates having wells to receive samples, for example, samples delivered by a robot. These microplates are made of molded plastic.

To enable remote identification of each microplate and to prevent any inversion or substitution, the microplate carries a radio-frequency circuit formed by an integrated or hybrid circuit enclosed in the mass at the time of molding.

This circuit comprises a radio-frequency transmitter associated with a memory in which is recorded the microplate identification information. Power can be provided by a battery or, preferably, by an induction coil. The signal transmitted by the transmitter is coded to enable a receiver associated with the analysis equipment to detect and identify the information recorded in the memory of the microplate that is in the detection zone. The information can be transmitted in a bidirectional manner.

This detection zone is limited to avoid disturbance by other microplates which might be close to the analysis equipment. This limitation is implemented by limiting the transmission power and possibly by the use of directional reception antennas or by any other anticollision process.

The information recorded in memory can be a unique identifier recorded in a read-only memory when the circuit is fabricated. The information can also be recorded at the time of first use, or at successive steps in the processing of the sample, for example, to ensure the traceability of successive tests. In this case, the electronic circuit also has a receiver associated with the recording means in the receiver of the information transmitted by a complementary device.

Activation of the transmission can be implemented by a circuit that detects a variation in the electromagnetic field, for example, by detecting the variation in the electric signal supplied by the induction coil. Variation in this signal triggers the transmission of a coded signal by the information recorded in the memory. This transmission can be renewed periodically, as long as the electric signal supplied by the induction coil remains superior to a threshold value.

Activation can also be implemented by the transmission of an activation signal by a transmitter provided in the analysis equipment. In this case, the electronic circuit of the receptacle must include a receiver for the detection of the activation signal.

What is claimed is:

1. A biological analysis system comprising:
   at least one receptacle of a biological sample to be analyzed;
   a part associated with the receptacle incorporating an electronic circuit comprising a memory and a contactless transmitter; and
   a biological analysis device comprising a receiver circuit, a comparator, and means to prevent operation in the absence of positive detection of a sample linked to an analysis, storage or operation to be performed, with positive detection being linked to an identification zone smaller than about 20 cm, wherein the comparator compares data transmitted by an electronic circuit incorporated in the part, with data transmitted by the circuit incorporated in the part pertaining to the analysis, storage or operation to be performed.

2. The biological analysis system according to claim 1, wherein the receptacle is a molded plastic part with an electronic circuit incorporated in its mass.

3. The biological analysis system according to claim 1, wherein the electronic circuit incorporated in the receptacle is an integrated circuit.

4. The biological analysis system according to claim 1, wherein the electronic circuit incorporated in the receptacle comprises an induction loop for powering the electronic circuit.

5. The biological analysis system according to claim 1, wherein the electronic circuit also comprises a receiver intended to receive personalization information recorded in an electronic memory.

6. The biological analysis system according to claim 5, wherein the analysis device comprises means for reading the signals transmitted by the receiver to provide the results of the analysis.

7. Biological analysis system comprising at least one receptacle of biological sample to be analyzed constituted by a part incorporating an electronic circuit comprising a memory and a contactless transmitter, and a biological analysis device comprising a receiver circuit and means for comparison between the data transmitted by the electronic circuit incorporated in the part, characterized in that the analysis device comprises means to prevent operation in the absence of positive detection of the sample linked to the analysis, storage or operation to be performed, with positive detection being linked to an identification zone smaller than 20 cm, with the data transmitted by the circuit incorporated in the part pertaining to the analysis, storage or operation to be performed.

8. Biological analysis system according to claim 7, characterized in that the receptacle is a molded plastic part with an electronic circuit incorporated in its mass.

9. Biological analysis system according to claim 7, characterized in that the electronic circuit incorporated in the receptacle for the sample to be analyzed is constituted by an integrated circuit.

10. Biological analysis system according to claim 7, characterized in that the electronic circuit incorporated in the receptacle for the sample to be analyzed comprises an induction loop for powering the electronic circuit.

11. Biological analysis system according to claim 7, characterized in that the electronic circuit also comprises a receiver intended for receiving personalization information recorded in the electronic memory.

12. Biological analysis system according to claim 7, characterized in that the analysis device comprises means for reading the signals transmitted by the receiver to provide the results of the analysis.

* * * * *